(12) United States Patent
Vardi

(10) Patent No.: US 8,123,768 B2
(45) Date of Patent: Feb. 28, 2012

(54) METHOD AND SYSTEM TO RESTRICT STOMACH SIZE

(76) Inventor: Gil Vardi, Town and Country, MO (US)

( * ) Notice: Subject to any disclaimer, the term of this patent is extended or adjusted under 35 U.S.C. 154(b) by 157 days.

(21) Appl. No.: 11/257,336

(22) Filed: Oct. 24, 2005

(65) Prior Publication Data

US 2007/0093861 A1 Apr. 26, 2007

(51) Int. Cl.
*A61B 17/08* (2006.01)
(52) U.S. Cl. ......... 606/153; 606/151; 606/139; 606/157
(58) Field of Classification Search ............ 606/139, 606/151, 153, 157, 144, 211, 219, 232; 623/1.13, 623/23.65
See application file for complete search history.

(56) References Cited

U.S. PATENT DOCUMENTS

| | | | |
|---|---|---|---|
| 4,616,656 A | | 10/1986 | Nicholson et al. |
| 5,320,632 A | * | 6/1994 | Heidmueller ................. 606/144 |
| 5,368,601 A | * | 11/1994 | Sauer et al. .................... 606/144 |
| 5,397,355 A | | 3/1995 | Marin et al. |
| 5,800,526 A | | 9/1998 | Anderson et al. |
| 5,865,791 A | * | 2/1999 | Whayne et al. ............... 604/500 |
| 6,036,699 A | * | 3/2000 | Andreas et al. ............... 606/139 |
| 6,113,609 A | * | 9/2000 | Adams ........................... 606/139 |
| 6,471,700 B1 | * | 10/2002 | Burbank et al. ................ 606/45 |
| 6,517,573 B1 | | 2/2003 | Pollock et al. |
| 6,572,629 B2 | | 6/2003 | Kalloo et al. |
| 6,755,869 B2 | * | 6/2004 | Geitz .......................... 623/23.65 |
| 7,033,384 B2 | * | 4/2006 | Gannoe et al. ................ 623/1.11 |
| 7,211,094 B2 | * | 5/2007 | Gannoe et ..................... 606/151 |
| 7,708,684 B2 | | 5/2010 | Demarais et al. |
| 2002/0183768 A1 | | 12/2002 | Deem et al. |
| 2003/0093117 A1 | * | 5/2003 | Saadat ........................... 606/221 |
| 2004/0092892 A1 | | 5/2004 | Kagan et al. |
| 2004/0122456 A1 | | 6/2004 | Saadat et al. |
| 2004/0122473 A1 | | 6/2004 | Ewers et al. |
| 2004/0148034 A1 | * | 7/2004 | Kagan et al. ................ 623/23.65 |
| 2004/0167546 A1 | | 8/2004 | Saadat et al. |
| 2004/0220682 A1 | | 11/2004 | Levine et al. |
| 2005/0192599 A1 | | 9/2005 | Demarais |
| 2005/0192601 A1 | | 9/2005 | Demarais |
| 2005/0203576 A1 | * | 9/2005 | Sulamanidze et al. ......... 606/228 |
| 2006/0036267 A1 | * | 2/2006 | Saadat et al. ................... 606/153 |

FOREIGN PATENT DOCUMENTS

WO 2007/051107 A2 5/2007

OTHER PUBLICATIONS

International Search Report, International App. No. PCT/US06/60192 (Sep. 11, 2007).

* cited by examiner

*Primary Examiner* — Ryan Severson
*Assistant Examiner* — Tin Nguyen
(74) *Attorney, Agent, or Firm* — Armstrong Teasdale LLP

(57) ABSTRACT

An implantable device for restricting a cross-sectional area of a cavity formed by a stomach wall includes a member. The member has a first end connected with respect to a first portion of the stomach wall and an opposing second end connected with respect to a second portion of the stomach wall. The member has shape memory properties and is adapted to move the first end towards the second end.

12 Claims, 7 Drawing Sheets

METHOD AND SYSTEM TO RESTRICT STOMACH SIZE

BACKGROUND OF THE INVENTION

This invention relates generally to gastric reduction and, more particularly, to restricting a cross-sectional area of a cavity formed by a stomach wall.

Morbid obesity is a major health concern in the United States and other countries. Morbid obesity commonly results in advancement of diseases and conditions, such as heart disease, hypertension, diabetes, heart failure and other related health complications.

Many treatments and surgical procedures have been developed for patients whose health and quality of life have suffered as a result of being morbidly obese. Conventional surgical procedures typically involve invasive procedures to permanently decrease the volume of the patient's stomach or bypass a portion of the stomach and/or small intestine.

BRIEF DESCRIPTION OF THE INVENTION

In one aspect, an implantable device for restricting a cross-sectional area of a cavity formed by a stomach wall is provided. The implantable device includes a member having a first end connected with respect to a first portion of the stomach wall and an opposing second end connected with respect to a second portion of the stomach wall. The member urges the first portion toward the second portion.

In another aspect, a system for restricting a cross-sectional area of a cavity formed by a stomach wall is provided. The system includes a catheter forming a passage. A first member is initially positioned within the passage and translatable with respect to the catheter along a length of the passage. A first fastener is connected to the first member. The first fastener is movable between a retracted configuration, in which the first fastener is at least partially disposed within the passage, and a deployed configuration, in which the first fastener is attached to a first portion of the stomach wall. A second member is also initially positioned within the passage and translatable with respect to the catheter along the length of the passage. A second fastener is connected to the second member. The second fastener is movable between a retracted configuration, in which the second fastener is at least partially disposed within the passage, and a deployed configuration, in which the second fastener is attached to a second portion of the stomach wall.

In another aspect, a method for restricting a cross-sectional area of a cavity formed by a stomach wall is provided. The method includes attaching a first fastener to a first portion of the stomach wall, attaching a second fastener to a second portion of the stomach wall, and urging the first portion towards the second portion to restrict the cross-sectional area of the cavity.

DETAILED DESCRIPTION OF THE INVENTION

Referring to FIGS. 1-18, the present invention is directed to a device and a system for closing or constricting an opening formed by a stomach wall, for example for restricting a cross-sectional area of a cavity formed by the stomach wall. Although the following description relates to constricting an opening formed by the stomach wall, the device and system of the present invention may be suitable for constricting other openings or orifices formed by or in a patient's body, as well as for connecting or attaching tissue and other body parts, for example.

Figure 1:
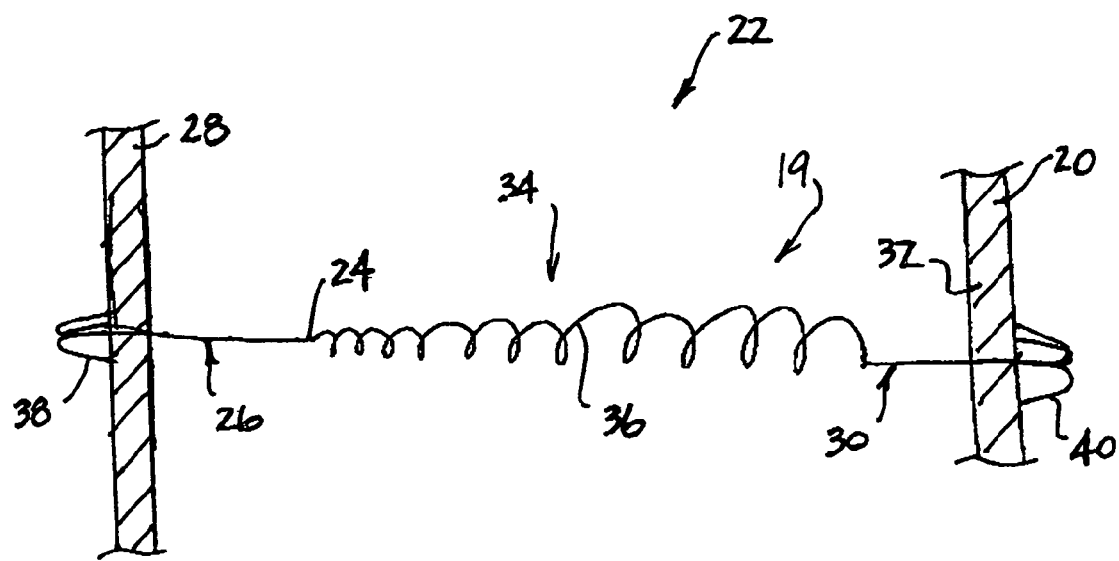
FIG. 1 is a partial sectional view of a stomach with a device for restricting a cross-sectional area of a cavity formed by the stomach attached to opposing portions of the stomach wall, according to one embodiment of the invention.

In one embodiment, an implantable device 19 for gastric reduction is shown in FIG. 1. Device 19 can be used to constrict an opening formed by a stomach wall 20, such as to restrict a cross-sectional area of a cavity 22 formed by the stomach wall. Device 19 includes a restricting and/or supporting member 24 having a first end 26 connectable or attachable to a first portion of the stomach wall, such as an anterior portion 28 of the stomach wall, and an opposing second end 30 connectable or attachable to a second portion of the stomach wall, such as a posterior portion 32 of the stomach wall. In one embodiment, first end 26 and second end 30 are attached or connected to generally opposing portions of the stomach wall. Alternatively, second end 30 may be generally radially offset with respect to first end 26 along an inner surface of the stomach wall forming the cavity.

Member 24 is preferably made of a biocompatible material including, without limitation, suitable metal materials, such as stainless steel, platinum, gold, titanium and nickel and/or composites or alloys thereof. In one embodiment, member 24 has shape memory properties and is adapted to move first end 26 towards second end 30. For example, in one embodiment, member 24 is made or fabricated from Nitinol. Nitinol possesses shape memory properties that allow the material to return to an initial configuration after a force applied to the material to shape, stretch, compress and/or deform the material is removed. It is apparent to those having ordinary skill in the art that member 24 may be made or fabricated using any suitable biocompatible materials, including suitable polymeric materials, preferably having suitable shape memory properties.

Member 24 may have any suitable size, shape and/or configuration, which provide sufficient structural strength required by the present invention. For example, in one embodiment, device 19 includes at least one member 24 shaped as a wire, tube or cylinder, as shown in FIG. 1. The wire, tube or cylinder has a generally circular cross-sectional area. Alternatively, or in addition, device 19 may include at least one member 24 having a generally rectangular cross-sectional area or any other suitable polygonal cross-sectional area.

As shown in FIG. 1, member 24 includes a body 34 extending between first end 14 and second end 16. In one embodiment, body 34 includes a biasing element 36, such as a spring or a coil, which exerts a biasing force, such as a tension force. With member 24 in a deployed configuration, in which first end 26 is secured to anterior portion 28 and second end 30 is secured to posterior portion 32 for example, biasing element 36 exerts a tension force at first end 26 and/or second end 30 sufficient to urge first end 26 towards second end 30 and, thus, urge anterior portion 28 of the stomach wall towards posterior portion 32 of the stomach wall to restrict the cross-sectional area of stomach cavity 22, as desired. In one embodiment, biasing element 36 is generally positioned at a mid-section of member 24 and provides a generally equal amount of force to first end 26 and second end 30. In alternate embodiments, biasing element 36 may be positioned on member 24 at a suitable location to provide a desired or selected force to first end 26 and/or second end 30.

In one embodiment, a first fastener 38 or other suitable connector connects or attaches first end 26 to the first portion of the stomach wall. Similarly, a second fastener 40, preferably the same or similar to first fastener 38, connects or attaches second end 30 to the second portion of the stomach wall. Each fastener 38, 40 is integrated with respective end 26, 30. Alternatively, fasteners 38, 40 are independent components attached or connected to member 24 using a suitable connector.

Fasteners 38, 40 may include any suitable attachment component to assist in attaching and/or securing fasteners 38, 40 with respect to the stomach wall. For example, fasteners 38, 40 include at least one flexible needle or hook each having a tip portion that extends through the stomach wall and is secured to an outer surface of the stomach wall, as shown in FIG. 1. In one embodiment, each fastener 38, 40 includes a plurality of hooks that are shapeable or bendable. Upon penetrating a thickness of the stomach wall, each hook extends radially outwardly to contact and/or interfere with an outer surface of the stomach wall and secure the respective end 26, 30 of member 24 with respect to the stomach wall. Alternatively, or in addition, fasteners 38, 40 may include a suture, staple or a suitable mechanical component that penetrates at least an inner surface of the stomach wall and extends at least partially through the stomach wall thickness.

In an alternative embodiment, implantable device 19 includes at least one magnet positioned with respect to each end 26, 30 of member 24. For example, a magnet is positioned at first end 26 and opposing second end 30 to magnetically urge first end 26 towards second end 30 and, thus, magnetically urge anterior portion 28 of the stomach wall towards posterior portion 32 of the stomach wall to restrict the cross-sectional area of stomach cavity 22, as desired. Alternatively, or in addition, each fastener 38, 40 includes a magnetic component that urges anterior portion 28 towards posterior portion 32 to restrict the cross-sectional area of stomach cavity 22, as desired.

Figure 2:
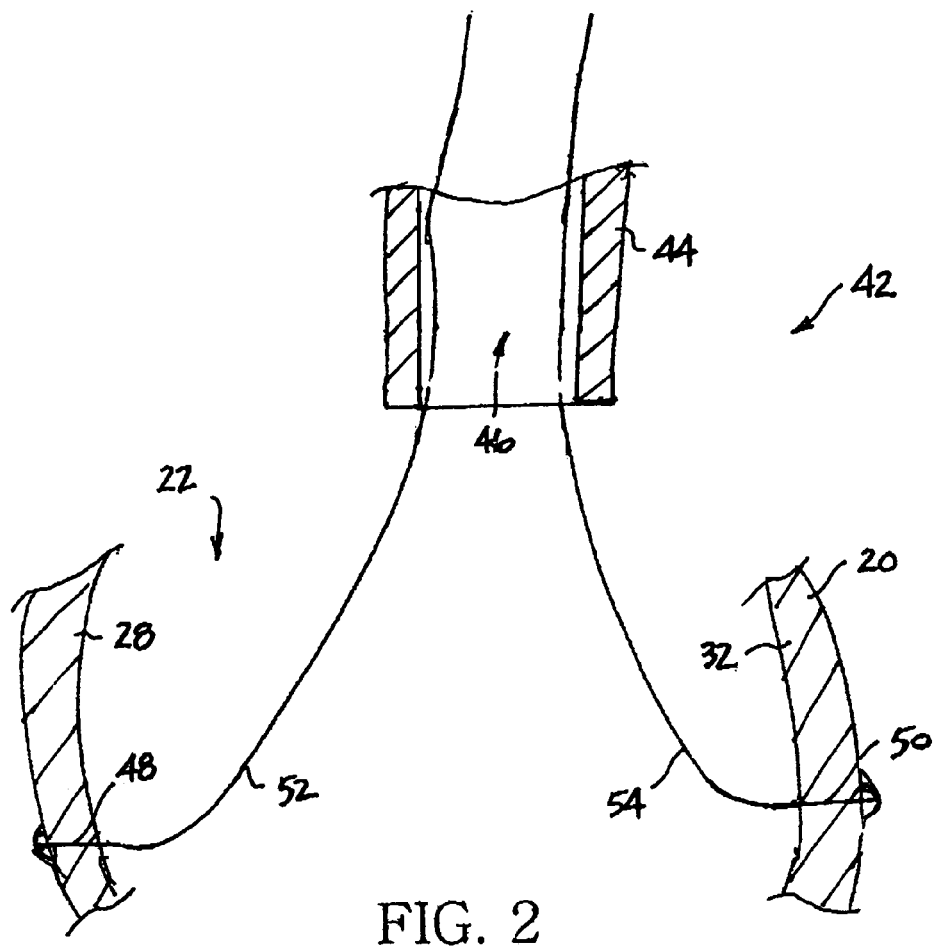
FIG. 2 is a partial sectional view of a stomach and a system for restricting a cross-sectional area of a cavity formed by the stomach, according to one embodiment of the invention.
Figure 3:
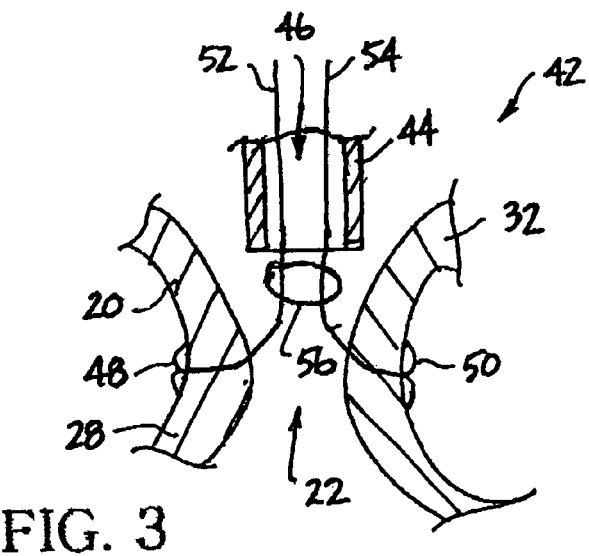
FIG. 3 shows the system of FIG. 2 with the stomach wall in a restricted position.

A system 42 for gastric reduction according to one embodiment is shown in FIGS. 2 and 3. System 42 is used to constrict an opening formed by stomach wall 20, such as to restrict a cross-sectional area of cavity 22 formed by the stomach wall. System 42 includes a catheter 44 forming a passage 46. In one embodiment, catheter 44 includes any suitable catheter component known to those skilled in the art and is introduced into a patient's body using any suitable or desirable method. For example, catheter 44 is directed through the patient's mouth and esophagus and into an opening formed by the stomach wall. Alternatively, as discussed in greater detail below, a catheter is introduced into the patient's stomach cavity percutaneously, e.g., by insertion through the patient's skin.

As shown in FIGS. 2 and 3, system 42 includes a first fastener 48 and an independent second fastener 50. Fasteners 48, 50 are at least partially positioned initially within passage 46 in a retracted configuration, to assist in the insertion of system 42 into the patient's body and stomach cavity. Upon introduction into the stomach cavity, each fastener 48, 50 is extended to connect to a portion of the stomach wall and movable to a deployed configuration to secure the fastener to the stomach wall. Preferably, fasteners 48, 50 are independently movable between the retracted configuration and the deployed configuration.

In one embodiment, fasteners 48, 50 are translatable with respect to catheter 44. Fastener 48 is movable from within passage 46 and attachable or connectable to a first portion of the stomach wall, such as anterior portion 28. Preferably, fastener 48 is connected or attached to a proximal end of a member 52 that is initially positioned within passage 46. Member 52 is preferably a suture or a wire that extends through passage 46 and is translatable with respect to catheter 44 along a length of passage 46.

Upon attachment to the first portion, fastener 48 is movable to the deployed configuration to secure attachment of fastener 48 to the first portion. Preferably, fastener 48 extends into and at least partially through a thickness of the stomach wall at the first portion. For example, as shown in FIG. 3, fastener 48 extends through the stomach wall and contacts an outer surface of the stomach wall to secure fastener 48 with respect to the first portion of the stomach wall. Fastener 48 may include any suitable attachment component to assist in attaching fastener 48 with respect to the first portion of the stomach wall. For example, fastener 48 includes at least one flexible needle or hook having a tip portion that extends or passes through the stomach wall and is secured to the outer surface of the stomach wall at the first portion. Alternatively, or in addition, fastener 48 includes a suture, a staple or other suitable mechanical component that penetrates at least an inner surface of the stomach wall. In an alternative embodiment, a magnet or a magnetic component is positioned with respect to each fastener 38, 40 to magnetically urge the first portion of the stomach wall towards the second portion of the stomach wall to restrict the cross-sectional area of stomach cavity 22, as desired.

Similarly, fastener 50 is movable from within passage 46 and attaches to a second portion of the stomach wall, such as posterior portion 32. Fastener 50 is preferably connected at a position on the inner surface of the stomach wall radially offset with respect to the position on the inner surface at which fastener 48 is attached to the stomach wall. In one embodiment, fastener 50 is attached to the stomach wall generally opposing fastener 48. Fastener 50 is at least partially positioned within passage 46 in an initial or retracted configuration for insertion into the stomach cavity. Within the stomach cavity, fastener 50 is extendable to a second portion of the stomach wall opposing the first portion of the stomach wall to which fastener 48 is connected.

In one embodiment, fastener 50 is connected to a proximal end of a member 54 that is initially positioned within passage 46. Member 54 is preferably a suture or wire that extends through passage 46 and is translatable with respect to catheter 44, independently of member 52, along a length of passage 46.

Figure 4:
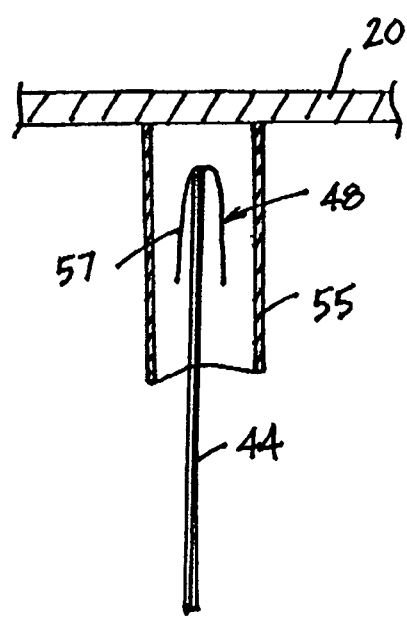
FIG. 4 is a partial sectional view of a stomach wall and a fastener initially positioned within a sheath, according to one embodiment of the invention.
Figure 5:
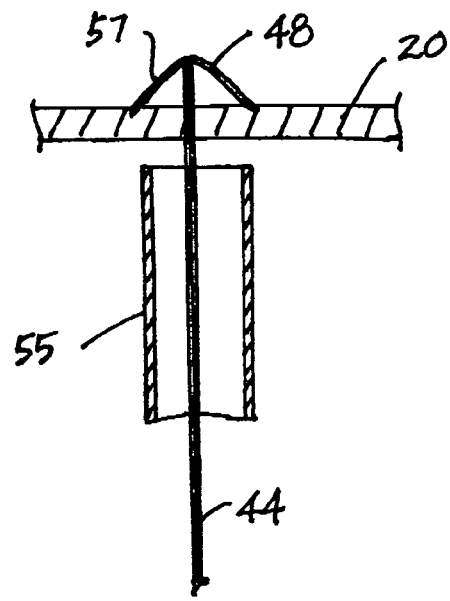
FIG. 5 shows the fastener of FIG. 4 in a deployed position and contacting the outer surface of the stomach wall.

In one embodiment, each fastener 48, 50 includes at least one flexible needle or hook that punctures and penetrates the stomach wall to contact the outer surface of the stomach wall and maintain a secure connection thereto. In the deployed configuration, each fastener 48, 50 is configured to curve or bend, for example as a result of the shape memory of the material used to fabricate the fasteners, to maintain each fastener 48, 50 securely positioned with respect to the stomach wall. In one embodiment, each fastener 48, 50 is initially positioned within a sheath 55 that maintains flexible hooks 57 of fasteners 48, 50 in the retracted position, as shown in FIG. 4. After fasteners 48, 50 penetrate the stomach wall, sheath 55 is movable along respective member 52, 54 to expose hooks 57. Each hook 57 moves to the deployed position, as a result of material shape memory for example, to contact the outer surface of the stomach wall and maintain a secure connection thereto, as shown in FIG. 5.

Figure 6:
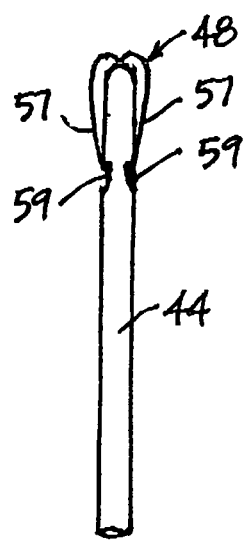
FIG. 6 shows a fastener initially positioned within a groove formed in a catheter, according to one embodiment of the invention.
Figure 7:
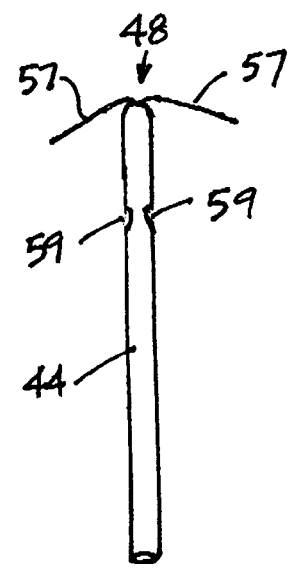
FIG. 7 shows the fastener of FIG. 6 in a deployed position.

In an alternative embodiment, each fastener 48, 50 is initially retained within a groove 59 formed in catheter 44, as shown in FIG. 6. After fasteners 48, 50 penetrate the stomach wall, hooks 57 are released from within groove 59 by a twisting motion of catheter 44. Each hook 57 moves to the deployed position to contact the outer surface of the stomach wall and maintain a secure connection thereto, as shown in FIG. 7. In alternative embodiments, any suitable retainer is used to retain hooks 57 within groove 59 with fasteners 48, 50 in the retracted position. Further, any suitable means known to those skilled in the art and guided by the teachings herein provided may be used to release hooks 57 from the retracted position, as desired.

With fasteners 48, 50 secured with respect to the stomach wall, catheter 44 is movable within the stomach cavity to urge fastener 48 toward fastener 50. For example, catheter 44 is movable along a length of each member 52, 54 to move fasteners 48, 50 together and, thus, urge the first portion of the stomach wall into proximity with the second portion of the stomach wall to close or restrict the cross-sectional area of the stomach cavity. Alternatively, members 52, 54 are pulled together with respect to catheter 44 to move fasteners 48, 50 together.

With fasteners 48, 50 moved together as desired, a retainer 56, such as a ring, a clip, a clamp, a collar or a suitable mechanical connector, is positioned with respect to fasteners 48, 50 to secure the first stomach wall portion in proximity with the second stomach wall portion and, thus, maintain the cross-sectional area of the stomach cavity in a restricted position, as shown in FIG. 3. In the restricted position, the patient is able control food intake, while satisfying his or her appetite and adhering to a dietary plan for losing weight and/or maintaining a healthy weight.

Figure 8:
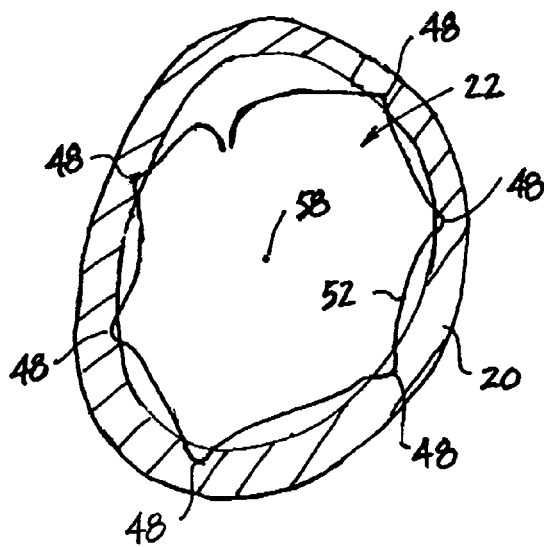
FIG. 8 is a sectional view of a stomach and a device for restricting a cross-sectional area of a cavity formed by the stomach, according to one embodiment of the invention.
Figure 9:
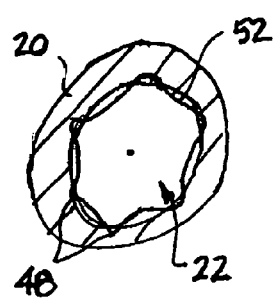
FIG. 9 shows the device of FIG. 8 with the stomach wall in a restricted position.
Figure 16:
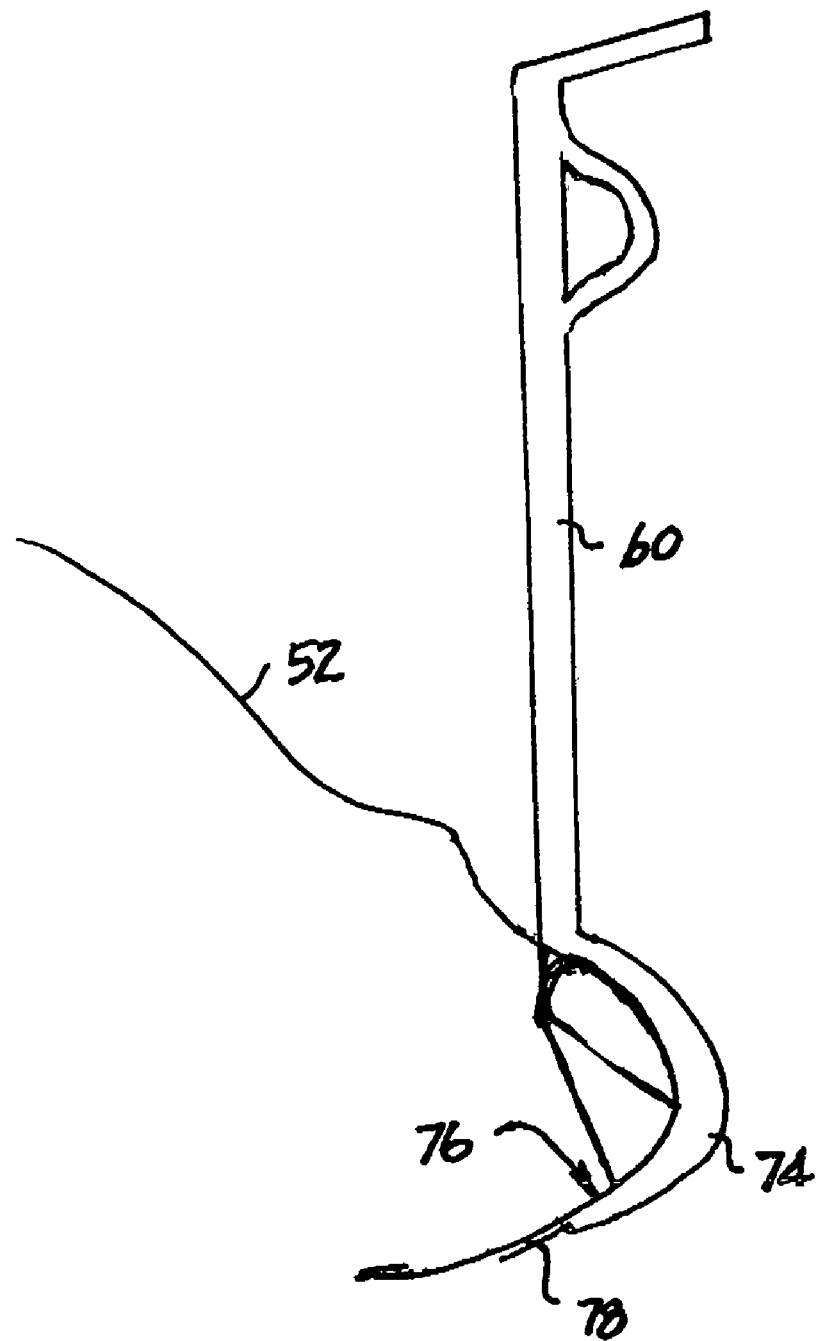
FIG. 16 is a front view of an instrument, according to one embodiment of the invention.

It is apparent to those skilled in the art that the system of the present invention may include any suitable number of fasteners. For example, as shown in FIGS. 8 and 9, in one embodiment, the system includes a plurality of fasteners 48 spaced about the inner surface of the stomach cavity and connected by member 52. By applying a pulling force to member 52, each fastener 48 is drawn or pulled toward a general center point 58 of cavity 22 to restrict the cross-sectional area of the stomach cavity, as shown in FIG. 9. A suitable mechanism or tool, such as a ratcheting tool or a wheel, not shown, may be used to pull member 52 so that fasteners 48 converge to decrease or restrict the cross-sectional area of the stomach cavity. Alternatively, a tool or instrument, such as instrument 60 shown in FIG. 16, is used to suture member 52 about the inner surface of the stomach wall with or without the use of fasteners.

Figure 10:
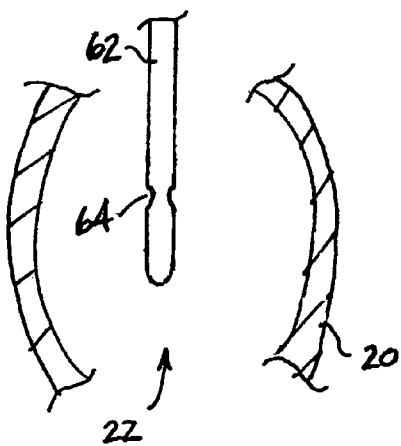
FIG. 10 is a sectional view of a stomach and a device for restricting a cross-sectional area of a cavity formed by the stomach, according to one embodiment of the invention.
Figure 11:
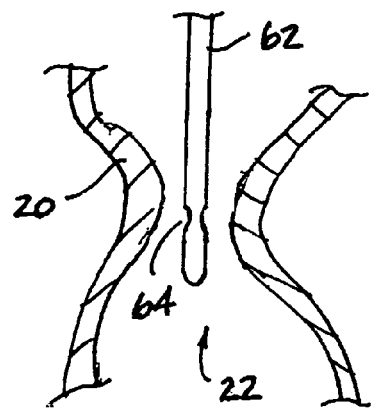
FIG. 11 shows the device of FIG. 10 with the stomach wall in a restricted position.

In an alternate embodiment, the cross-sectional area of the stomach cavity is restricted by applying a suction force to constrict the stomach wall. For example, a suitable suction device 62, preferably having a plurality of apertures 64 to provide a suitable or desired suction force, is positioned within cavity 22, as shown in FIGS. 10 and 11. Upon applying a suction force to the stomach wall, portions of the stomach wall are drawn inwardly and the cross-sectional area of stomach cavity 22 is restricted, as shown in FIG. 11. With the suction force applied, member 24 and/or fasteners 48, 50, for example, are connected to the stomach wall to maintain the stomach wall in the restricted position. Alternatively, or in addition, the drawn-in portion of the stomach wall is sutured, wired or stapled, for example, to maintain the stomach wall in the restricted position.

As briefly discussed above, in an alternate embodiment, system 42 is introduced into the patient's stomach cavity percutaneously, to restrict the size of a patient's stomach and/or constrict an opening formed by the stomach wall. Preferably, system 42 is introduced into the stomach cavity with the assistance or guidance of an endoscope 66. Endoscope 66 is inserted into the stomach cavity through the patient's esophagus. A light emitted from endoscope 66 is visible through the skin to allow the doctor to see the impression of the percutaneously-introduced catheter 44 on the stomach wall.

Figure 12:
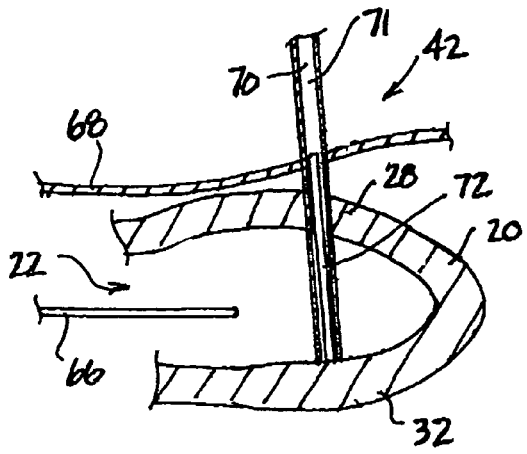
FIG. 12 is a partial sectional view of a patient's body and a device percutaneously inserted into the patient's stomach for restricting a cross-sectional area of a cavity formed by the stomach, according to one embodiment of the invention.
Figure 13:
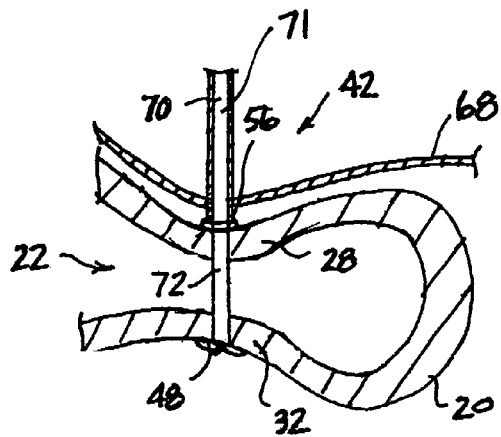
FIG. 13 shows the device of FIG. 12 with the stomach wall in a restricted position.

FIGS. 12 and 13 show a device percutaneously inserted into a patient's stomach for restricting a cross-sectional area of a cavity formed by the stomach. In this embodiment, catheter 70 penetrates a patient's skin 68 and a first portion of the stomach wall, preferably anterior portion 28. Catheter 70 proceeds through stomach cavity 22 and penetrates an opposing second portion of the stomach wall, preferably posterior portion 32. As shown in FIG. 13, a catheter passage 71 accepts a fastener 48 during introduction of system 42 into the stomach cavity. Upon insertion of catheter 70 into the stomach cavity, fastener 48 punctures and penetrates at least an inner surface of the stomach wall and is connected to posterior portion 32.

Fastener 48 preferably includes a plurality of shapeable needles or hooks that extend through the thickness of posterior portion 32 and contact the outer surface of the stomach wall at posterior portion 32. A rod 72 is slidably positioned within passage 71 and connected to fastener 48. With fastener 48 secured to posterior portion 32, a retainer 56, such as a clip, a clamp, a collar or a ring, is positioned about an outer periphery of rod 72 and is slidably movable along a length of rod 72 to move anterior portion 28 towards posterior portion 32 and restrict cavity 22. With anterior portion 28 positioned relative to posterior portion 32, retainer 56 maintains rod 72 in position. Alternatively, a fastener, such as fastener 50, attaches rod 72 to anterior portion 28. In one embodiment, an excess or unused portion of rod 72 is detached and removed from the patient's body, along with catheter 70, to complete the procedure.

Figure 14:
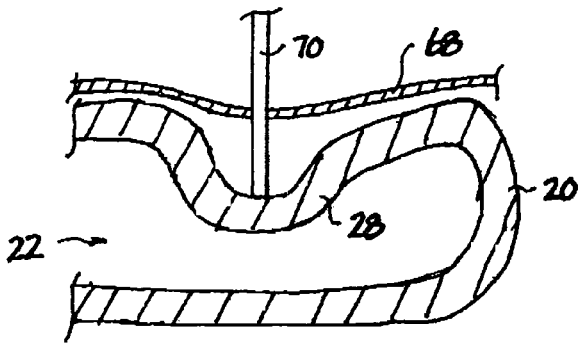
FIG. 14 is a partial sectional view of a patient's body and a device percutaneously inserted into the patient's body for restricting a cross-sectional area of a cavity formed by the stomach wall, according to one embodiment of the invention.
Figure 15:
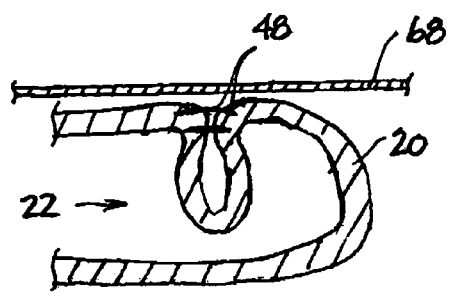
FIG. 15 shows the device of FIG. 14 with the stomach wall in a restricted position.

In an alternate embodiment, system 42 is introduced percutaneously without entering into the patient's stomach cavity to restrict the size of a patient's stomach. Referring to FIGS. 14 and 15, catheter 70 penetrates a patient's skin 68. A suitable force is applied to catheter 70 to depress a portion of the stomach wall, such as anterior portion 28, without puncturing and/or otherwise damaging the outer surface of the stomach wall. As anterior portion 28 is depressed, adjacent portions of the stomach wall converge about catheter 70. The adjacent portions of the stomach wall are connected using a suitable fastener 48, such as a plurality of hooks, staples and/or sutures to restrict the stomach cavity size. Catheter 70 is removed from the patient's body to complete the procedure.

As shown in FIG. 16, surgical instrument 60 is used with device 19 and/or system 42 of the present invention. Instrument 60 includes a distal end portion 74 preferably having an arcuate or semi-circular shape that forms a channel 76 extending at least partially along a length of distal end portion 74. Member 52, or any suitable suturing piece, is positioned within channel 76 and movable within channel 76 with respect to distal end portion 74. A shapeable needle 78 is movably positioned at distal end portion 74 and within channel 76 to allow needle 78 to move in a reciprocating motion with respect to distal end portion 74. As needle 78 reciprocates, needle 78 enters and exits the stomach wall to form a hole therethrough while feeding member 52 through the formed hole. In one embodiment, instrument 60 is utilized to form a plurality of holes about the inner surface of the stomach wall and feed member 52 through the formed holes. Member 52 is then drawn or pulled to converge portions of the stomach wall and restrict a cross-sectional area of the cavity formed by the stomach wall.

Figure 17:
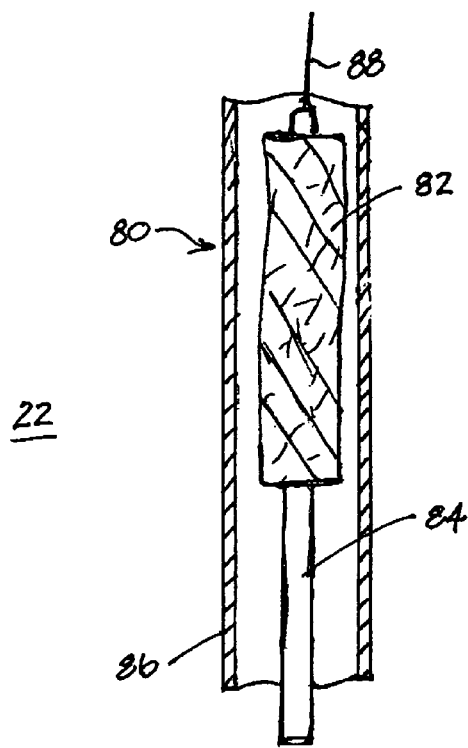
FIG. 17 is a partial sectional view of a device for restricting a cross-sectional area of a cavity formed by the stomach, according to one embodiment of the invention.
Figure 18:
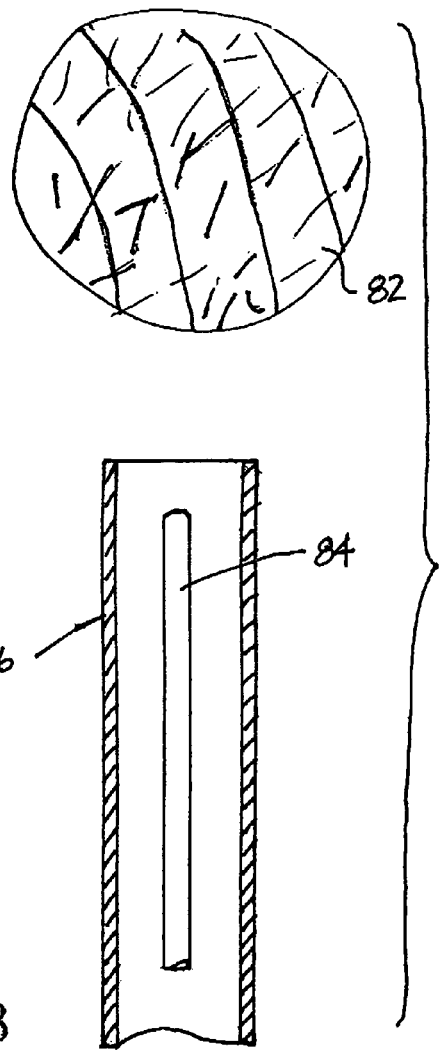
FIG. 18 shows the device of FIG. 17 in an expanded configuration.

FIGS. 17 and 18 show a device 80 that is inserted into a patient's stomach for restricting a cross-sectional area of a cavity formed by the stomach. In one embodiment, device 80 includes an expandable member 82 that is initially positioned in a collapsed position about or within a catheter 84, as shown in FIG. 17. A sheath 86 is positioned about member 80 and at least a portion of catheter 84. In the collapsed position, device 80 is directed into the patient's stomach cavity 22. In one particular embodiment, device 80 is directed into cavity 22 using a suitable guide wire 88. Upon introduction of device 80 into cavity 22, sheath 86 is movable along a length of catheter 84 to expose member 82. Within cavity 22, member 82 expands, as shown in FIG. 18, to restrict a cross-sectional area of cavity 22. In one embodiment, a balloon is used to expand member 82. Member 82 increases in volume to expand to a generally spherical shape having a hollow interior. In alternative embodiments, member 82 has a generally solid interior in the expanded configuration. Further, in alternative embodiments, member 82 has any suitable expanded shape.

In this embodiment, member 82 is fabricated using a Nitinol skeleton including a covering cloth. In alternative embodiments, member 82 includes the skeleton without the covering cloth. Further, member 82 may be fabricated using a suitable biocompatible material known to those skilled in the art and guided by the teachings herein provided.

While the invention has been described in terms of various specific embodiments, those skilled in the art will recognize that the invention can be practiced with modification within the spirit and scope of the claims.

What is claimed is:

1. A system for restricting a cross-sectional area of a cavity formed by a stomach wall, said system comprising:
   a delivery sheath;
   a catheter within said delivery sheath, said catheter comprising a passage extending therethrough;
   a first member initially positioned within said passage and movable with respect to said catheter along a length of said passage;
   a first fastener extending from a proximal end of said first member, said first fastener movable between a retracted configuration and a deployed configuration, in the deployed configuration said first fastener attachable to a first portion of the stomach wall;
   a second member initially positioned within said passage and movable with respect to said catheter along a length of said passage; and
   a second fastener extending from a proximal end of said second member, said second fastener movable independent of said first fastener between a retracted configuration and a deployed configuration, in the deployed configuration said second fastener attachable to a second portion of the stomach wall, wherein said catheter comprises a plurality of grooves extending partially inward from an outer surface of said catheter without providing communication with said passage, said plurality of grooves retaining distal ends of said first and second fasteners on said outer surface of said catheter when said fasteners are in the retracted configuration and said catheter is within said delivery sheath, said catheter twistable to release said distal ends from said grooves to urge said fastener to the deployed configuration when said catheter is beyond said delivery sheath.

2. A system in accordance with claim 1, wherein said first fastener comprises a plurality of flexible hooks, each flexible hook of said plurality of flexible hooks retained within a corresponding groove of said plurality of grooves when said first fastener is in the retracted configuration.

3. A system in accordance with claim 1 wherein each of said first member and said second member is independently translatable with respect to a length of said catheter to move one of said first fastener and said second fastener in said deployed configuration with respect to a center point of the cross-sectional area of the cavity.

4. A system in accordance with claim 1 wherein said first fastener is configured to be attached to the stomach wall at a first position radially offset with respect to a second position of said second fastener.

5. A system in accordance with claim 1 wherein, in said deployed configuration, each of said first fastener and said second fastener configured to extend through the stomach wall and contact an outer surface of the stomach wall.

6. A system in accordance with claim 1 wherein each of said first fastener and said second fastener comprises at least one of a needle, a hook, a staple and a suture.

7. A system in accordance with claim 1 further comprising a first magnet positioned with respect to said first fastener and a second magnet positioned with respect to said second fastener, said first magnet and said second magnet configured to move said first fastener toward said second fastener and restrict the cross-sectional area of the cavity when said first fastener and said second fastener are in said deployed configuration.

8. A system for restricting a cross-sectional area of a cavity formed by a stomach wall, said system comprising:
- a delivery sheath;
- a catheter within said delivery sheath, said catheter comprising a passage extending therethrough;
- a first member initially positioned within said passage and movable with respect to said catheter along a length of said passage;
- a first fastener extending from a proximal end of said first member, said first fastener movable between a retracted configuration and a deployed configuration, in the deployed configuration said first fastener attachable to a first portion of the stomach wall;
- a second member initially positioned within said passage and movable with respect to said catheter along a length of said passage;
- a second fastener extending from a proximal end of said second member, said second fastener movable independent of said first fastener between a retracted configuration and a deployed configuration, in the deployed configuration said second fastener attachable to a second portion of the stomach wall;
- a plurality of grooves defined in an outer surface of said catheter, each groove of the plurality of grooves extending partially inward from an outer surface of said catheter without providing communication with said passage, and retaining a respective end of said first fastener and said second fastener in the respective retracted configuration when said catheter is within said delivery sheath, said catheter twistable to release said respective end of said first fastener and said second fastener from each groove to urge said first fastener and said second fastener to the respective deployed configuration when said catheter is beyond said delivery sheath; and
- a retainer member configured to move along, and relative to, said first fastener and said second member and restrict the cross-sectional area of the cavity when said first fastener and said second fastener are in the respective deployed configuration.

9. A method for restricting a cross-sectional area of a cavity formed by a stomach wall, said method comprising:
- twisting a first member to release distal ends of a first fastener from a first groove of a plurality of grooves to urge the first fastener to deployed configuration when a catheter is beyond a delivery sheath, the first groove extending partially inward from an outer surface of the catheter without providing communication with a passage defined by the catheter, the first groove retaining the distal ends on the outer surface when the first fastener is in a retracted configuration and the catheter is within the delivery sheath;
- attaching the first fastener to a first portion of the stomach wall;
- twisting a second member to release distal ends of a second fastener from a second groove of the plurality of grooves to urge the second fastener to a deployed configuration independent of the first fastener when the catheter is beyond the delivery sheath, the second groove extending partially inward from an outer surface of the catheter without providing communication with a passage defined by the catheter, the second groove retaining the distal ends on the outer surface when the second fastener is in a retracted configuration and the catheter is within the delivery sheath;
- attaching the second fastener to a second portion of the stomach wall;
- urging the first portion towards the second portion to restrict the cross-sectional area of the cavity; and
- maintaining the first portion urged towards the second portion to secure the cavity in a restricted position.

10. A method in accordance with claim 9 further comprising:
- inserting a catheter into the cavity, the catheter initially housing the first member and the second member; and
- removing the catheter from within the cavity upon attachment of the first fastener to the first portion and attachment of the second fastener to the second portion to urge the first portion towards the second portion, and restrict the cross-sectional area of the cavity.

11. A method in accordance with claim 9 further comprising:
- inserting a catheter percutaneously through an anterior portion of the stomach wall;
- attaching the first fastener to an opposing posterior portion of the stomach wall;
- pushing a collar against an outer surface of the anterior portion to urge the anterior portion towards the posterior portion to restrict the cross-sectional area of the cavity; and
- attaching at least one of the second fastener, a suture and a clip to the anterior portion.

12. A system for use with a delivery sheath to restrict a cross-sectional area of a cavity formed by a wall, said system comprising:
- a catheter positionable within the delivery sheath, said catheter comprising a passage extending therethrough and a plurality of grooves extending partially inward from an outer surface of said catheter without providing communication with said passage,
- a first member initially positioned within said passage and movable with respect to said catheter along a length of said passage;
- a first fastener extending from a proximal end of said first member, said first fastener movable between a retracted configuration and a deployed configuration, in the deployed configuration said first fastener attachable to a first portion of the wall, wherein said plurality of grooves retain distal ends of said first fastener on said outer surface of said catheter when said first fastener is in the retracted configuration and said catheter is within said delivery sheath, and said catheter is twistable to release said distal ends from said plurality of grooves to urge said first fastener to the deployed configuration when said catheter is beyond said delivery sheath;
- a second member initially positioned within said passage and movable with respect to said catheter along a length of said passage; and
- a second fastener extending from a proximal end of said second member, said second fastener movable independent of said first fastener between a retracted configuration and a deployed configuration, in the deployed configuration said second fastener attachable to a second portion of the wall, wherein said plurality of grooves retain distal ends of said second fastener on said outer surface of said catheter when said second fastener is in the retracted configuration and said catheter is within said delivery sheath, and said catheter is twistable to release said distal ends from said plurality of grooves to urge said second fastener to the deployed configuration when said catheter is beyond said delivery sheath.

* * * * *